US008405836B2

(12) United States Patent
Yablon

(10) Patent No.: US 8,405,836 B2
(45) Date of Patent: Mar. 26, 2013

(54) SYSTEM AND METHOD FOR MEASURING AN OPTICAL FIBER

(75) Inventor: Andrew D. Yablon, Livingston, NJ (US)

(73) Assignee: Interfiber Analysis, LLC, Livingston, NJ (US)

( * ) Notice: Subject to any disclaimer, the term of this patent is extended or adjusted under 35 U.S.C. 154(b) by 432 days.

(21) Appl. No.: 12/728,147

(22) Filed: Mar. 19, 2010

(65) Prior Publication Data

US 2011/0228260 A1 Sep. 22, 2011

(51) Int. Cl.
*G01N 21/41* (2006.01)
(52) U.S. Cl. .................. 356/517; 356/73.1; 356/479
(58) Field of Classification Search ............ 356/73.1, 356/479, 481, 497, 504, 517
See application file for complete search history.

(56) References Cited

U.S. PATENT DOCUMENTS

| 4,361,402 | A | * | 11/1982 | Costa | 356/73.1 |
| 4,365,449 | A | * | 12/1982 | Liautaud | 52/28 |
| 4,391,516 | A | | 7/1983 | Boggs et al. | |
| 7,352,474 | B2 | | 4/2008 | Bachim et al. | |
| 2009/0125242 | A1 | * | 5/2009 | Choi et al. | 702/19 |

OTHER PUBLICATIONS

D. Marcuse, "The Transverse Interferometric Method (TIM)" Principles of Optical Fiber Measurements, 1981, Chapter 4, pp. 150-161, Academic Press, New York, USA.
M. Sochacka, "Optical Fibers Profiling by Phase-Stepping Transverse Interferometry," IEEE Journal of Lightwave Technology, 1994, pp. 19-23, vol. 12, No. 1, IEEE, Piscataway, NJ, USA.
P. L. Chu and T. Whitbread, "Nondestructive determination of the refractive index profile of an optical fiber: fast Fourier transform method," Applied Optics, 1979, pp. 1117-1122, vol. 18, No. 7, OSA, Washington, DC, USA.
G. A. Dunn and D. Zicha, "Using the DRIMAPS System of Transmission Interference Microscopy to Study Cell Behavior," Cell Biology A Laboratory Handbook 2nd edition, 1998, pp. 44-53, vol. 3, Academic Press, New York, USA.
M. R. Hutsel et al, "Algorithm performance in the determination of the refractive-index profile of optical fibers," Applied Optics, 2008, pp. 760-767, vol. 47, No. 6, OSA, Washington, DC, USA.
H. M. Presby and I. P. Kaminow, "Binary silica optical fibers: refractive index and profile dispersion measurements," Applied Optics, 1976, pp. 3029-3036, vol. 15, No. 12, OSA, Washington, DC, USA.
A. Yang et al, Measuring the refractive indices of liquids with a capillary tube interferometer, Applied Optics, 2006, pp. 7993-7998, vol. 45, No. 31, OSA, Washington, DC, USA.
F. El-Diasty, "Characterization of optical fibers by two- and multiple-beam interferometry," Optics and Lasers in Engineering, 2008, pp. 291-305, vol. 46, No. 4, Elsevier, Ltd., Amsterdam, Holland.
A. D. Yablon, "Refractive Index Profiling of Fibers and Fusion Splices," Optical Fiber Fusion Splicing, 2005, pp. 199-202, Springer, New York, USA.
A. D. Yablon, "Multi-Wavelength Optical Fiber Refractive Index Profiling by Spatially Resolved Fourier Transform Spectroscopy," IEEE Journal of Lightwave Technology, 2010, pp. 360-364, vol. 28, No. 4, IEEE, Piscataway, NJ, USA.

(Continued)

*Primary Examiner* — Tarifur Chowdhury
*Assistant Examiner* — Jonathon Cook
(74) *Attorney, Agent, or Firm* — Berkeley Law & Technology Group, LLP

(57) ABSTRACT

Subject matter disclosed herein relates to measuring optical fibers or measuring devices comprising optical fibers and, in particular, to measuring a variation of refractive index of an optical fiber as a function of position and wavelength.

22 Claims, 6 Drawing Sheets

OTHER PUBLICATIONS

A. D. Yablon, "Multi-Wavelength Optical Fiber Refractive Index Profiling by Spatially Resolved Fourier Transform Spectroscopy," OFC/NFOEC, 2009, Postdeadline paper PDPA2, OSA, Washington, DC. USA.

A. D. Yablon, "Multiwavelength optical fiber refractive index profiling," Fiber Lasers VII: Technology, Systems, and Applications, 2010, proceedings of the SPIE vol. 7580, paper No. 40, SPIE, Bellingham, WA, USA.

P. Hariharan, "Modified Mach-Zehnder Interferometer," Applied Optics, 1969, pp. 1925-1926, vol. 8, No. 9, OSA, Washington, DC, USA.

L. M. Boggs et al, "Rapid Automatic Profiling of While-Fiber Samples: Part I," Bell System Technical Journal, 1979, pp. 867-882, vol. 58, No. 4, AT&T, New York, USA.

H. M. Presby et al, "Rapid Automatic Profiling of While-Fiber Samples: Part II," Bell System Technical Journal, 1979, pp. 883-902, vol. 58, No. 4, AT&T, New York, USA.

B. L. Bachim and T. K. Gaylord, "Microinterferometric optical phase tomography for measuring small, asymmetric refractive-index differences in the profiles of optical fibers and fiber devices," Applied Optics, 2005, pp. 316-327, vol. 44, No. 3, OSA, Washington, DC, USA.

B. L. Bachim, T. K. Gaylord, and S. C. Mettler, "Refractive-index profiling of azimuthally asymmetric optical fibers by microinterferometric optical phase tomography," Optics Letters, 2005, pp. 1126-1128, vol. 30, No. 10, OSA, Washington, DC, USA.

\* cited by examiner

SYSTEM AND METHOD FOR MEASURING AN OPTICAL FIBER

BACKGROUND

1. Field

Subject matter disclosed herein relates to measuring optical fibers or measuring devices comprising optical fibers and, in particular, to measuring a variation of refractive index of an optical fiber as a function of position and wavelength.

2. Information

Optical fibers may be used for applications as diverse as telecommunications links, diagnostic and therapeutic medical systems, high-power lasers and amplifiers, or environmental sensing. These diverse applications have driven development of a diversity of optical fiber types and designs. However, in such cases, a parameter affecting optical performance of an optical fiber may comprise a spatial distribution of its refractive index or a spectral dependence of its refractive index distribution.

BRIEF DESCRIPTION OF THE DRAWINGS

Non-limiting and non-exhaustive embodiments will be described with reference to the following figures, wherein like reference numerals refer to like parts throughout the various figures unless otherwise specified.

DETAILED DESCRIPTION

Reference throughout this specification to "one embodiment" or "an embodiment" means that a particular feature, structure, or characteristic described in connection with an embodiment is included in at least one embodiment of claimed subject matter. Thus, appearances of the phrase "in one embodiment" or "an embodiment" in various places throughout this specification are not necessarily all referring to the same embodiment. Furthermore, particular features, structures, or characteristics may be combined in one or more embodiments.

In an embodiment, a system for measuring refractive index of an optical fiber as a function of spatial position and optical wavelength may comprise a two beam interferometer and a digital computer to execute particular instructions for analyzing information acquired by the interferometer. An embodiment may provide cost or convenience benefits including that an interferometer may be readily constructed from commercially available optical components.

Figure 1:
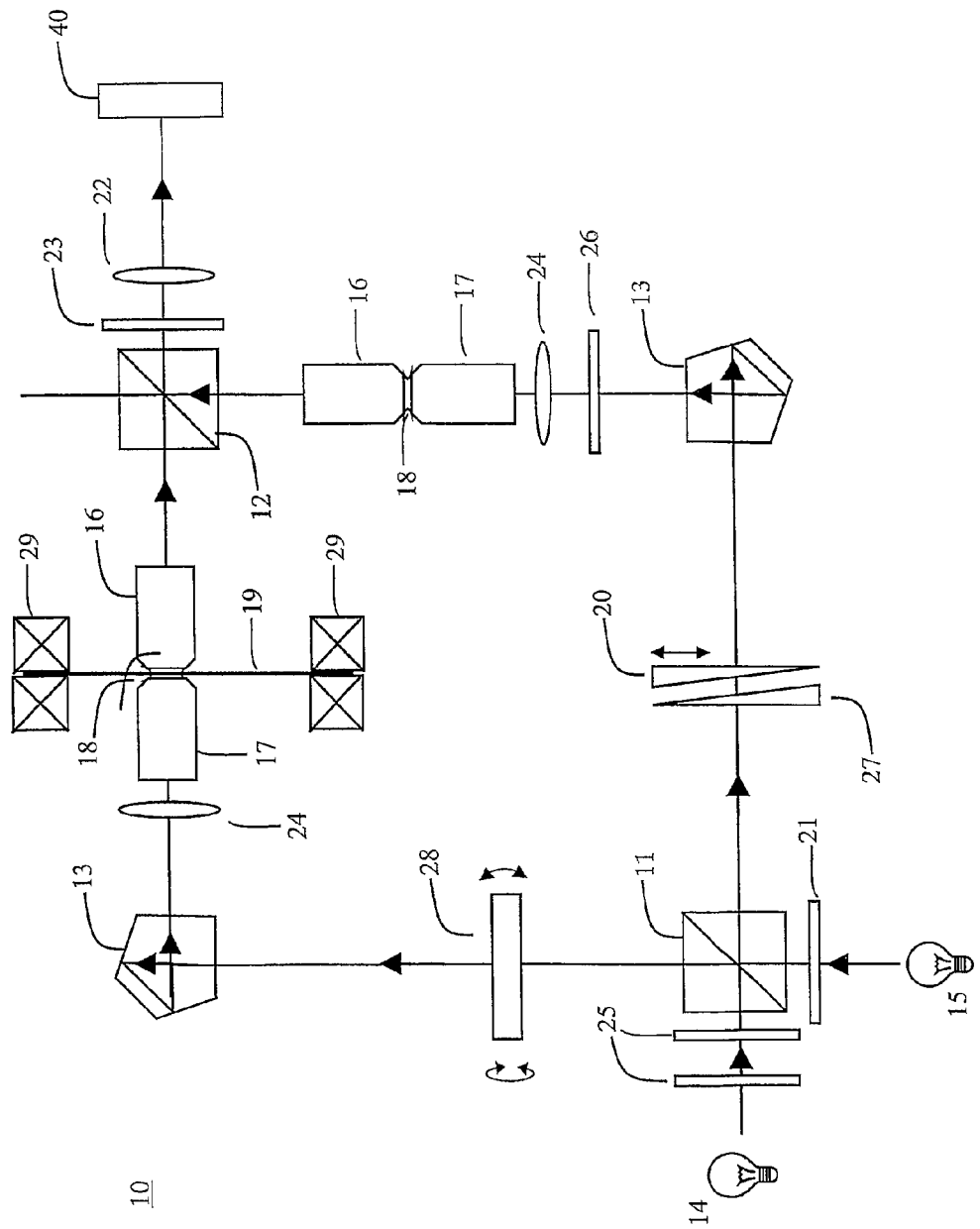
FIG. 1 is a schematic diagram of a Mach-Zehnder interferometer, according to an embodiment.

FIG. 1 is a schematic diagram of a two beam Mach-Zehnder interferometer 10, according to an embodiment. A two beam Mach-Zehnder interferometer may comprise a cube beam splitter 11 and a cube beam combiner 12, which may be illuminated by a broad-band optical source, such as an incandescent light bulb, for example. Alternatively, an arc lamp or a source formed from one or more light-emitting diodes (LEDs) may be used for illumination. Interferometers may be sensitive to ambient temperature changes. An incandescent light source may at least partially be thermally isolated from an interferometer using, for example, an optical fiber bundle (not shown) to transmit incandescent light emission to an input port of an interferometer. An incandescent light source may be contained in a separate housing (not shown) from an interferometer to reduce thermal effects of a light source on an interferometer. In an implementation, an interferometer, or at least a portion of an optical beam path of an interferometer, may be encapsulated to reduce effects of air currents or temperature non-uniformities from adversely affecting operation.

As shown in FIG. 1, multiple input ports of beam splitter 11 may be concurrently or simultaneously used to illuminate interferometer 10 using multiple optical sources. Source bandwidth may be broadened as a result. For example, a visible wavelength source 14 may be combined with a near infrared source 15 using beam splitter 11. Near infrared source 15 may comprise an incandescent source transmitting through one or more spectral filters 21 that may block visible radiation during near infrared radiation transmission, for example. Visible wavelength source 14 may comprise an incandescent source transmitting through one or more spectral filters 25 that may block near-infrared radiation during visible radiation transmission, for example. Beam splitter 11, which may comprise a cube beam splitter, for example, or beam combiner 12 may be operable across a spectrum for which measurements are to be performed. Ultra-broadband measurements comprising visible and near-infrared illumination may benefit from a cube beam splitter incorporating a partially silvered reflecting surface that is generally more effective over a broader spectral range than all-dielectric beam splitters. Of course, details of interferometer 10 are merely examples, and claimed subject matter is not so limited.

In a particular implementation, substantially identical pentaprisms 13 may be used instead of 90-degree deflecting mirrors. Compared to mirrors, pentaprisms may more easily facilitate alignment of an interferometer and may also provide a relatively convenient approach for balancing optical path lengths of interferometer arms. For example, if one of the pentaprisms shown in FIG. 1 is translated in the plane of the interferometer along the direction of the pentaprism's plane of symmetry, the pentaprism may extend or contract length of its associated optical path without substantially perturbing alignment of interferometer 10. This feature may lead to relatively high contrast fringes obtained from broad band illumination. Such high contrast fringes may result, at least in part, from optical path lengths of both arms of an interferometer being nearly identical. Reflecting surfaces of pentaprisms 13 may be coated with protected aluminum or protected silver to provide relatively efficient reflection across a broad spectral band.

In an alternative embodiment, one or more pentaprisms 13 may be replaced with a pair of mirrors (not shown), heretofore called "pentaprism equivalent elements," positioned such that reflecting surfaces of the mirrors may deflect an interferometer beam through substantially the same angles as the reflecting surfaces of said pentaprisms. Translating a pair of mirrors along its plane of symmetry may extend or contract length of its associated optical path without substantially perturbing alignment of interferometer 10.

In one implementation, two substantially identical infinity-adjusted oil-immersion objective lenses 16 may be positioned substantially equal distances away from a tube lens 22. Of course, particular types of lenses are merely examples, and claimed subject matter is not limited in this respect. Tube lens 22 may be positioned about one focal length away from an active surface of a broadband array detector 40. A detector may comprise a CCD (charge coupled device) array or CMOS (complementary metal oxide semiconductor) array. An object plane of an infinity-adjusted objective lenses may be imaged onto an active surface of an array detector located at an image plane. In one implementation, broadband array detector 40 may comprise a digital camera incorporating a computer controllable exposure setting to improve available dynamic range. Oil-immersion objective lenses may be chromatically adjusted over a spectral band for which measurements are to be performed. If a chromatic adjustment bandwidth of an oil-immersion lenses does not cover a desired bandwidth of measurements, interference fringes may be defocused over at least a portion of a measurement spectrum and fine features, such as a small diameter optical fiber core, may be blurred over spectral regions, for example. This limitation may be addressed by making more than one measurement, and illuminating interferometer 10 with a subset of a spectral band that may be sufficiently narrow so that objective lenses are adequately adjusted over that subset of the spectrum. For example, an objective lens may be adjusted so that its optical aberrations may be substantially reduced over a range of 400 nm to 700 nm, whereas measurement data may be desired over the range of 400 nm to 1000 nm. An objective lens may be used to make separate measurements with an illumination source comprised of light from 400 nm to 700 nm, from 700 nm to 800 nm, from 800 nm to 900 nm, or from 900 nm to 1000 nm.

Two substantially identical oil-immersion condenser lenses 17 may be positioned in opposition to objective lenses 16. A relatively small quantity of refractive index matching liquid 18 may be held between a tip of condenser lens 17 and a tip of an opposing objective lens 16 by surface tension. A relatively small volume of refractive index matching liquid may be maintained in position. A refractive index of a liquid may be selected to be close to that of a fiber under test, which may be approximately 1.46 for silica fibers, for example. Of course, a refractive index may be higher or lower. For example, if cladding of a fiber under test is doped or if a fiber is comprised of a non-silica glass or of a plastic material, an index of refraction of a fiber under test may fall within a fairly wide range. In another implementation, condenser lenses 17 may comprise commercially available oil-immersion objective lenses, or may be substantially identical to objective lenses 16. Alternatively, a condenser lenses may comprise a singlet lens mounted at one end of a tube with a planar optical window mounted at the other end.

A portion of a fiber sample 19 to be measured may be positioned inside refractive index matching liquid 18 held between opposing condenser and objective lenses in one arm of interferometer 10, heretofore referred to as the sample arm. It is understood that fiber sample 19 may comprise a segment of two fibers spliced together, an optical fiber grating, an optical fiber coupler, a tapered segment of optical fiber, or an optical fiber bundle, for example. Fiber sample 19 may be held in place by chucks 29 that may grip the fiber sample on one or both sides of an interferometer beam path. For example, the axis of the fiber sample may coincide with the direction of gravity (e.g., vertically oriented) in which case the fiber sample may be gripped at its higher end so the remaining portion of the (hanging) fiber sample may be kept substantially straight by gravity. A fiber sample may be rotated about its axis and measurements may be performed at discrete angular orientations, for example. Although fiber sample 19 in FIG. 1 is shown oriented in the plane of an interferometer, orientation is not so limited. For example, a fiber sample may be rotated such that its axis is oriented at any transverse orientation relative to an interferometer probe beam. Advantages of an orientation of a fiber sample being angled out of the plane of an interferometer may include that a fiber sample may be employed that is arbitrarily long. To maintain signal quality or integrity of a relatively fragile or rigid sample fiber, the fiber sample may be maintained fairly straight. An orientation may also lead to at least partially avoiding a lost or excessively attenuated (e.g., by bending losses) optical signal being carried by a sample fiber.

In one embodiment, a computer operated phase shifter 20 may apply a relative phase shift to one arm of interferometer 10 and acquire measurement information from array detector 40. In a particular implementation, a relative phase shift may be applied at a substantially constant rate. In another particular implementation, phase shifter 20 may apply a continual or a continuous phase shift to one interferometer arm relative to the other interferometer arm. For example, phase shifter 20 need not be idle during measurements. One method for applying a continuous phase shift may comprise translating one of pentaprisms 13 along its axis of symmetry in the plane of interferometer 10. Alternatively, translating optical wedge 20 may also produce a relative phase shift. Two substantially identical optical wedges 20 and 27 may be inserted into one arm of interferometer 10 and an optical window 28 whose thickness very nearly matches total thickness of the wedges may be inserted into the other arm of interferometer 10, resulting in substantially equal optical path lengths. Wedge angles may be on the order of 10 to 30 arc minutes. Wedged windows may comprise commercially available optical components. If one of the two optical wedges 20 is translated laterally across a light beam of an interferometer arm, a relative phase shift may be imparted to that beam. As a result, fringes may be seen to evolve or modulate at array detector 40, heretofore termed "fringe modulation." For example, a wedge comprised of BK7 optical glass with a wedge angle of 30 arc minutes may produce a relative optical path length shift of 20 microns corresponding to approximately 40 waves of 500 nm wavelength visible light if a wedge is laterally translated about 4 mm. A mechanical micrometer-adjusted translation stage or computer controlled stepper motor or DC servo motor may be used to translate one of optical wedges 20 or 27, for example. In one implementation, a wedge may be translated a single time in a single direction to accomplish a single measurement scan. In another implementation, multiple scans may be accomplished passing a wedge across an interferometer beam multiple times in substantially the same direction or by oscillating a position of the wedge in alternating directions.

In one implementation, condenser lenses 24 may be placed in an optical path of interferometer 10 if condenser lenses 17 are substantially similar or identical to objective lenses 16, but are not required. Condenser lenses 24 may allow condenser lenses 17 to more fully illuminate an object plane so that interferometer fringes may be detected over a field of array detector 40. As indicated above, an array detector may comprise a CCD array or a CMOS camera. For convenience, in the description below, array detector 40 may be described as a CCD array, though claimed subject matter is not so limited. Interferometer alignment and, hence, fringe contrast obtained at a CCD array, may be improved by pivoting planar window 28 in either axis shown in FIG. 1 so as to shear an illuminating beam of one arm relative to an illumination beam of the other arm. Angle and spacing of resulting fringes at a CCD array may be affected by pivoting beam combiner 12 or beam splitter 11.

A polarizer 23 may be included between beam combiner 12 and tube lens 22 to affect polarization of light detected at a CCD array. Alternatively, or in addition, a polarizer may be included between a light source and beam splitter 11. A polarizer may be desirable if birefringence or residual stress of an optical fiber is to be measured. Optical filters to reduce spectrum detected at an array detector may also be positioned between beam combiner 12 and array detector 40.

A dispersion compensating element 26 may comprise a relatively thin sheet of glass, such as a microscope cover slip, which may be added to either or both arms of interferometer 10 to improve fringe contrast. Although pentaprisms 13 may be translated to compensate for small differences in optical path length between two interferometer arms, their translation may not compensate for variation of optical path length with optical wavelength (dispersion).

Experiments have shown that microscope cover slips selected from industry standard thickness size 0, 1, 1.5, 2, or 3 may improve fringe contrast obtained from broad band illumination. Accordingly, trial and error may be involved in a process to select a microscope cover slip and to determine whether to place it in a reference or sample arms of interferometer 10.

Figure 2:
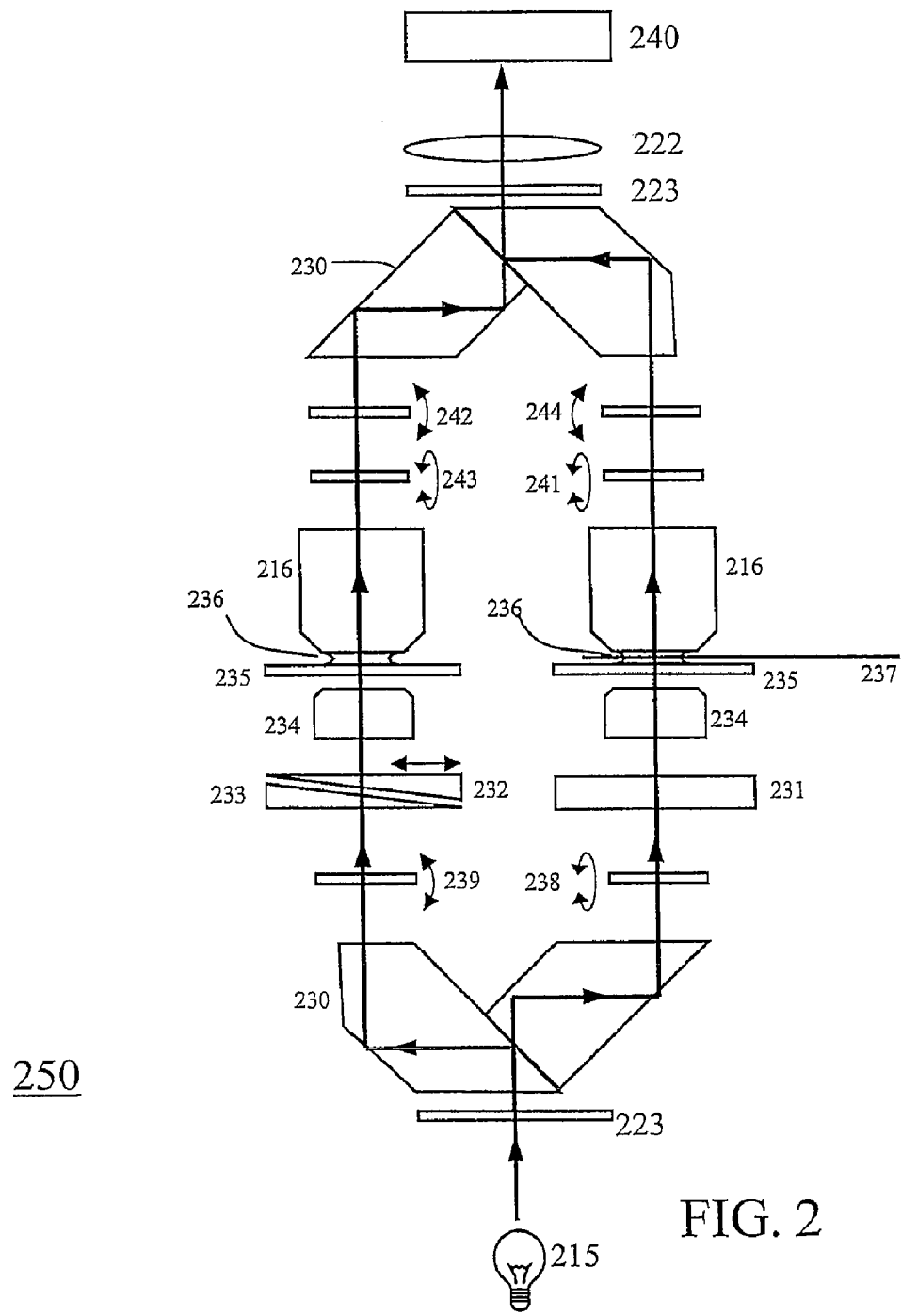
FIG. 2 is a schematic diagram of a Mach-Zehnder interferometer, according to another embodiment.

FIG. 2 is a schematic diagram of a Mach-Zehnder interferometer 250, according to another embodiment. Interferometer 250, which may be illuminated using a broadband source 215, for example, may involve a matching pair of custom optical components 230 to perform a dual role of beam splitter (or beam combiner) and beam displacement. Furthermore, interferometer 250 may involve relatively flat glass substrates 235 to constrain refractive index matching liquid 236. Compared to interferometer 10, interferometer 250 may provide a more limited operational range to at least partially compensate for path length differences between two interferometer arms via moving wedge 232 and tilting plates 241-244 compared to translating pentaprisms 13 in FIG. 1.

In an embodiment, interferometer 250 may include refractive index matching liquid 236 held in place by surface tension between glass planar substrates 235 and identical oil-immersion objective lenses 216 in both interferometer arms. A polarizer 223 may be used between beam combining/displacing prism 230 and tube lens 222 or between optical source 215 and beam splitting/displacing prism 230 to affect the polarization, for example, if measuring birefringence or residual stress. A portion of a fiber sample 237 to be measured may be positioned inside refractive index matching liquid 236 held between glass plate 235 and objective lens 216. Condensers 234 need not be coupled to a fiber sample using refractive index matching liquid. A translating optical wedge 232 may be used with a stationary wedge 233, and a compensating plate 231 as a phase shifter, for example. Fringe contrast may be improved by adjusting an angle of tilting plates 238 or 239. Relative optical path length between two arms, angle of the fringes observed on array detector 240, or spacing between fringes may be adjusted by tilting optical plates 241-244. Unlike translating pentaprisms 13 shown in FIG. 1, tilting optical plates 241-244 may not adjust total optical path length difference without also perturbing fringe spacing.

Although embodiments described above may provide refractive index measurements across a broad optical band, in some cases refractive index measurements may be desired over a relatively narrow spectral range or at a specific wavelength that lies inside an available spectral band. In this case, signal-to-noise ratio (S/N) at desired wavelength(s) may be elevated in the following manner. For example, returning to FIG. 1, by inserting a spectral filter passing desired wavelength(s) between light source 14 and beam splitter 11 or between beam combiner 12 and tube lens 22, array detector 40 may detect fringes corresponding to the filter's spectrum. As a result, S/N ratio at desired wavelength(s) may be increased. In this case a system may function as a narrow bandwidth optical fiber measurement system, but with wavelength adjustability.

Figure 4:
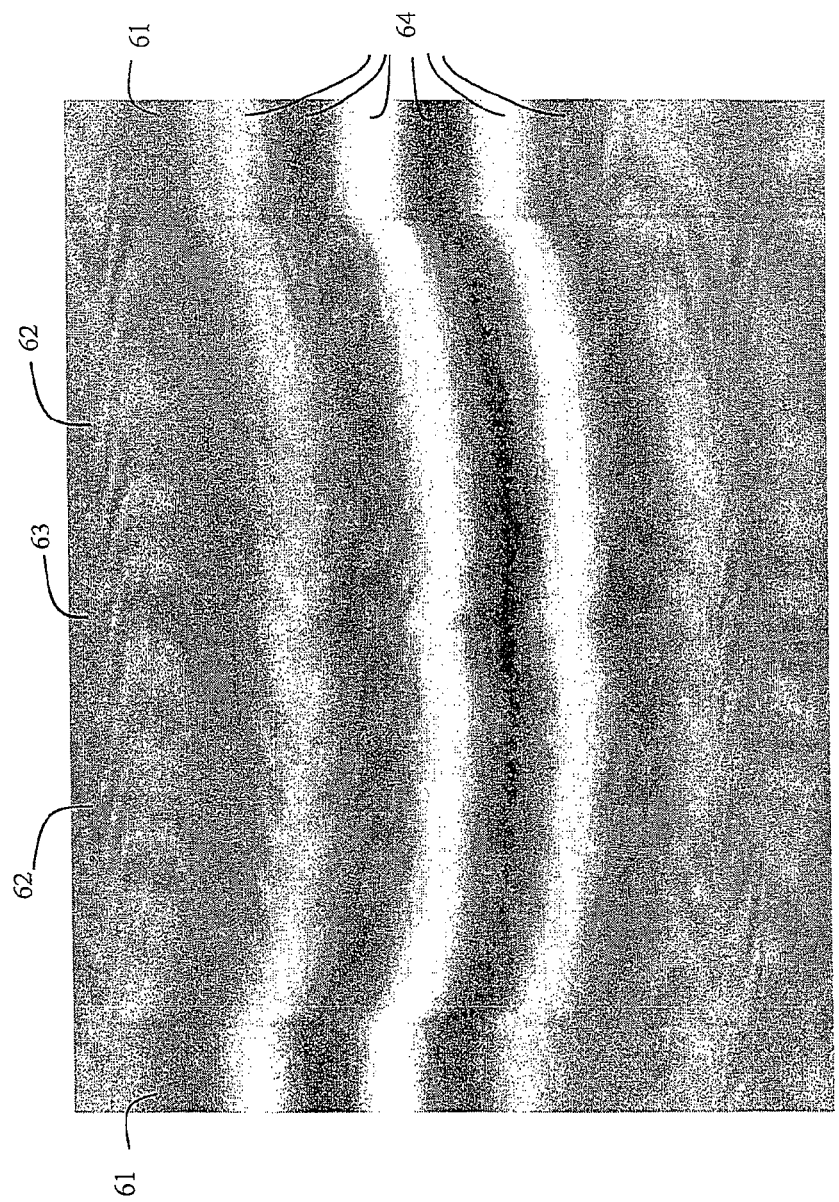
FIG. 4 is a sample interferogram image, according to an embodiment.

If translating optical wedge 20 to produce a relative phase shift, relatively small non-uniformities in a velocity profile may perturb measured phase extracted during a Fourier analysis. It may be relatively difficult or expensive to construct a drive system that may achieve optical wedge translation having nearly uniform velocity. Fortunately, embodiments of interferometric systems described herein may be inherently more robust to velocity non-uniformities compared to other instruments, such as a Fourier transform spectrometer, for example. One reason for this difference may be because embodiments of interferometric systems described herein may measure relative phase between neighboring pixels of array detector, rather than absolute phase or absolute magnitude. Interferometric systems discussed above may be made robust to velocity non-uniformities by employing fringes falling on an array detector that run perpendicular to the axis of a fiber sample. A radial position of a fiber sample may thus experience a diversity of phase, as shown in a sample interferogram image frame in FIG. 4. Several interference fringes 64 are seen to run substantially horizontally across the fiber sample and the surrounding refractive index matching fluid 61, which is oriented vertically in the image. A core region 63 lies in the center of the fiber sample surrounded by cladding 62. Averaging over diversity of phases (for example, averaging vertical columns of pixels in FIG. 4) may provide additional robustness to possibly unavoidable wedge velocity non-uniformities, thereby permitting use of low-cost off-the-shelf stepper motors or DC servomotors to actuate an optical wedge mounted to low-cost off-the-shelf translation stages. Of course, details of a measured fiber sample are merely examples, and claimed subject matter is not so limited.

In an implementation, transverse dimension of a fiber under test may exceed an active area at an image plane of an array detector. A fiber may be positioned so that measurements may be acquired for one side of the fiber. Following this, the fiber may be laterally translated to image the other side of the fiber. The relative phase for sides may be digitally stitched together so that an effective area of the array detector available for fiber measurement may be larger than the actual array detector area. In general, this approach may also be used to map variations in refractive index along a structure whose axial dimension may exceed available area of an array detector.

Figure 3:
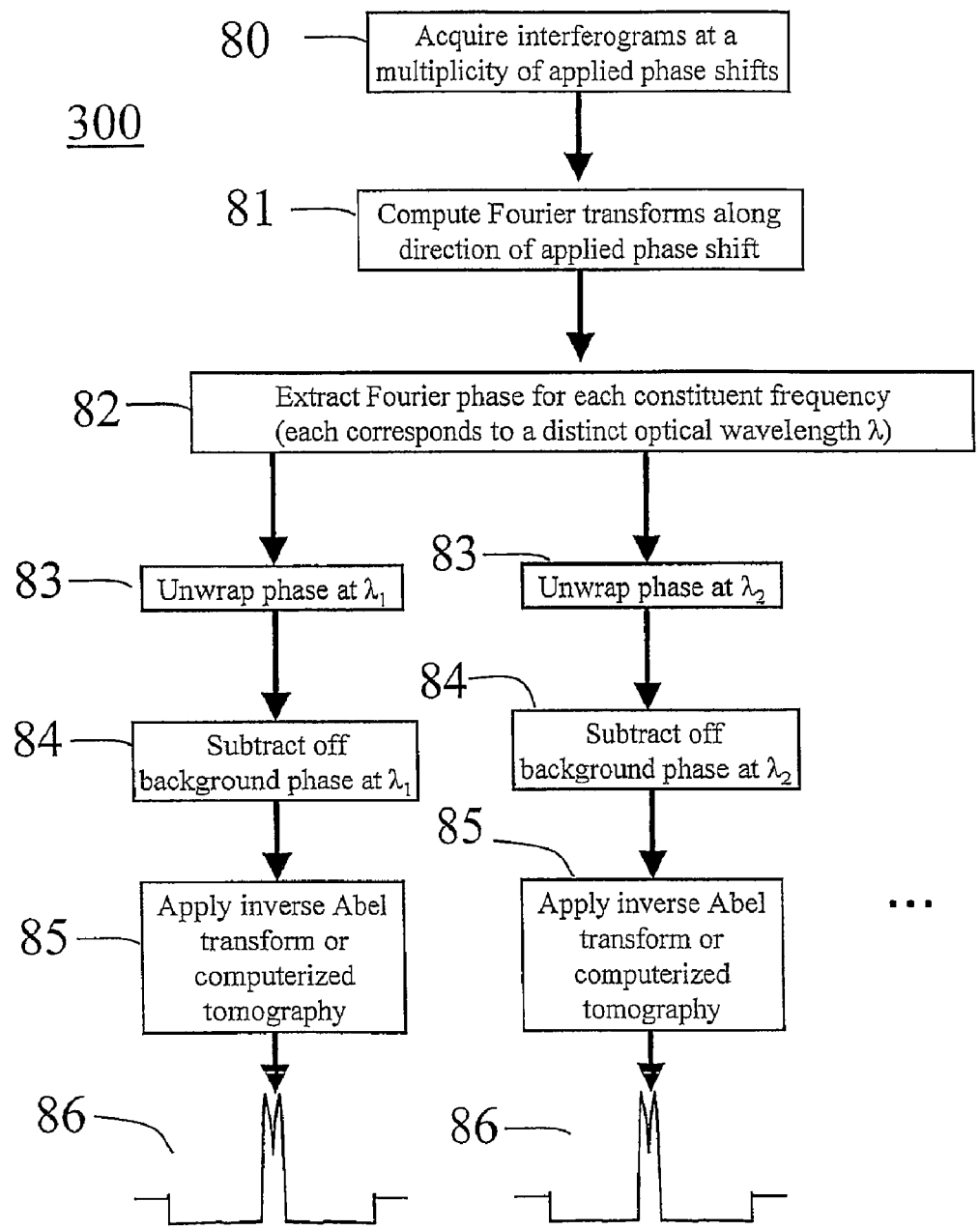
FIG. 3 is a flow diagram of a process to determine a refractive index profile using information acquired from an array detector, according to an embodiment.

FIG. 3 shows a flow diagram of a process 300 to determine a refractive index profile using information acquired from an array detector, according to an embodiment. In one implementation, a process may be carried out by a digital computer executing particular code, for example. At block 80, measurement information, such as brightness values, may be acquired by a computer from an array detector at a multiplicity of applied phase shifts. At block 81, spectral decomposition may be accomplished by applying a Fourier transform, for example the Fast Fourier transform (FFT), to brightness values associated with pixels of an array detector in the direction of applied phase shift. An increment of applied phase shift between sequential brightness values may be substantially constant to facilitate application of an FFT, but if this is not the case, interpolation may be performed to obtain regularly spaced measurement information prior to application of an FFT. In one embodiment, brightness values from local groups of pixels may be averaged or otherwise combined together to reduce noise or increase signal brightness and a Fourier transform may be applied. It is understood that in this context groups of pixels may themselves be referred to as pixels without loss of generality.

At block 82, an output signal from application of Fourier transform may comprise a phase angle for a pixel at constituent Fourier frequencies. According to one embodiment shown in FIG. 3, subsequent processing for a multiplicity of different Fourier frequencies may be substantially similar. Individual Fourier frequencies may be associated with a particular optical frequency comprising interferometer illumination. A relationship may be established either by a calibration process or by computation based, at least in part, on knowledge of total optical path length incurred if traversing a phase shifter. One way to perform an empirical calibration of a relationship may be to perform measurements using a narrowband optical filter situated between illumination source 14 and beam splitter 11 or between beam combiner 12 and tube lens 22, as shown in FIG. 1. A peak in a detected power spectrum may reveal which Fourier frequency corresponds to wavelengths passed by the optical filter. A relationship between Fourier frequency and optical wavelength may be precisely mapped out by carrying out a calibration procedure with a relatively large number of distinct narrowband optical filters, for example. In general, optical frequency of an interferometer illumination may be approximately linearly proportional to a Fourier frequency. A two-dimensional array of complex magnitude and complex phase corresponding to a particular Fourier frequency may comprise a relative optical intensity and relative optical phase, respectively, at a particular interferometer illumination frequency (or wavelength).

According to the Nyquist criterion of digital signal processing, sampling frequency is to be at least twice a maximum frequency of the signal. Therefore, a spatial frequency of interferogram am acquisition with respect to applied phase shift may be at least twice a highest spatial frequency of a broad band source. Thus, for a 400 to 900 nm incandescent source, interferograms may be acquired at least every 200 nm of applied optical path length phase shift. For a 30 arc-minute wedge phase shifter described above, this corresponds to an interferogram acquisition for 40 microns of wedge transverse displacement, for example.

Phase angle for individual pixels or group of pixels at constituent frequencies may be determined by a Fourier transform computation to modulo $2\pi$. At block 83, a difference in phase between neighboring pixels or groups of pixels at optical wavelengths may be unwrapped using any of a number of known phase unwrapping procedures. If a portion of measurement information includes a spatial region where no optical fiber sample is present, phase unwrapping may determine total optical path through a sample relative to this region, which may serve as an arbitrary background reference. Imperfections in an interferometer may produce systematic variations of interferogram phase as a function of pixel location. Measurement accuracy may be improved by subtracting variations. For example, accuracy may be improved by acquiring two sets of measurement information, one with a sample fiber present and another without a sample fiber, and subsequently subtracting an unwrapped phase of measurement information acquired without a sample from an unwrapped phase acquired with the sample, as at block 84.

In an embodiment, optical path length at a given optical probe frequency and at a given pixel location may comprise the real part of a refractive index of a sample integrated over a path length of a particular probe ray that travels across the sample to that pixel location. Therefore, at block 85, measurement information processing may involve inverting this integration, heretofore termed "numerical inversion," to reveal a refractive index as a function of location at an optical wavelength inside an optical fiber sample 86. This inversion may be accomplished in at least one of two ways, depending on symmetrical properties of the optical fiber sample.

If a fiber sample exhibits some amount of rotational symmetry about its central axis, various procedures for the inverse Abel transform may be applied to integrated optical path length measurement information at a particular optical probe frequency to convert an optical path length measurement into a refractive index as a function of radial position. If a fiber sample exhibits some amount of rotational asymmetry about its central axis (for example, a polarization-maintaining optical fiber), computerized tomography may be used to convert integrated optical path length measurement information into refractive index as a function of position in the fiber sample. Separate information may be acquired at a multiplicity of relative rotation angles between the optical fiber and an interferometer, for example. Processes described at blocks 80-84 of FIG. 3 may be applied to signal information acquired at discrete rotation angles. To reduce time to acquire or process measurement information, measurement information may be acquired over a relatively small range of rotation angles. For example, a refractive index profile of a substantially non axi-symmetric fiber, such as a polarization maintaining fiber, may be determined from interferometer measurements made approximately every 5 degrees from 0 to 175 degrees of rotation (e.g., 36 interferometer measurements in an optical fiber rotation range less than 180 degrees). Interferometer data need not be taken over angles greater than 180 degrees and may be taken over an angular range of less than 180 degrees. Of course, details of a measurement are merely examples, and claimed subject matter is not so limited.

Figure 6:
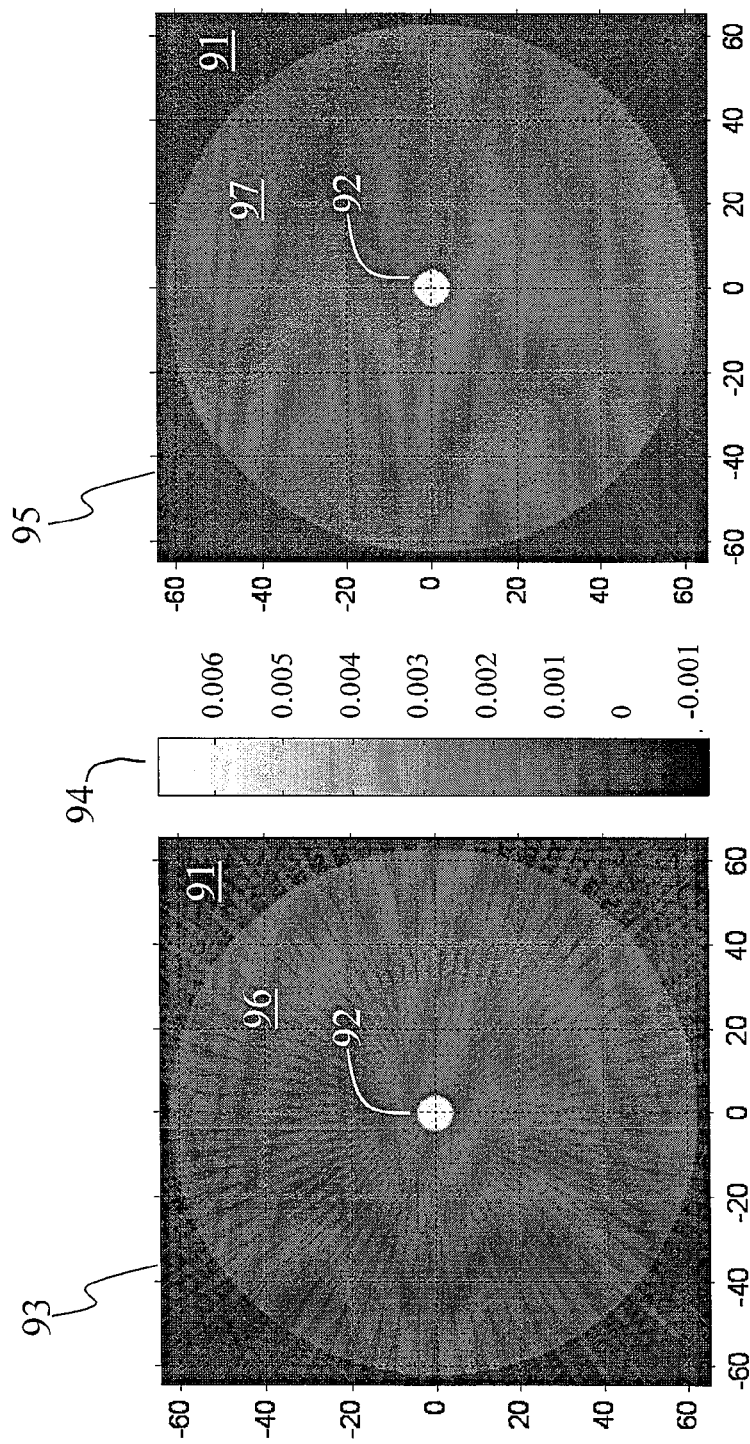
FIG. 6 shows plots of tomographic scans of an optical fiber before and after azimuthal filtering, according to an embodiment.

To further reduce time for measurement information acquisition or processing, it may be advantageous to reduce a total number of interferometer measurements used for computerized tomography by using a relatively coarse angular interval of 5 degrees or greater. A coarse angular interval may exhibit numerical artifacts in the azimuthal direction, especially far from the center of rotation, as shown in chart 93 in FIG. 6. Charts 93 and 95 show measured refractive index as a function of both transverse coordinates in a fiber sample, represented as the horizontal and vertical axes of the charts. The two transverse coordinates in the fiber are assumed to have their origin at the center of the fiber's core. Brightness scale 94 in FIG. 6 shows a measured refractive index relative to surrounding refractive index matching oil 91 for signal information with azimuthal artifacts 93 and for filtered signal information to remove azimuthal artifacts 95. While measurement artifacts are small in fiber core 92 they are larger in fiber cladding 96 if no azimuthal filtering is performed. Fan-like numerical artifacts evident in fiber cladding 96 may be reduced or suppressed by filtering measured signal information in the azimuthal direction to affect frequencies corresponding to these artifacts. Spatial frequencies to be reduced or suppressed may be harmonics of the number of discrete fiber rotation angles used for interferometer measurement acquisition. For example, in an embodiment comprised by 36 measurements every 5 degrees from 0 to 175 degrees, spatial frequencies of 36, 72, and 144 in the azimuthal direction may be filtered out of measurement information to yield reduced artifacts in cladding region 97.

Figure 5:
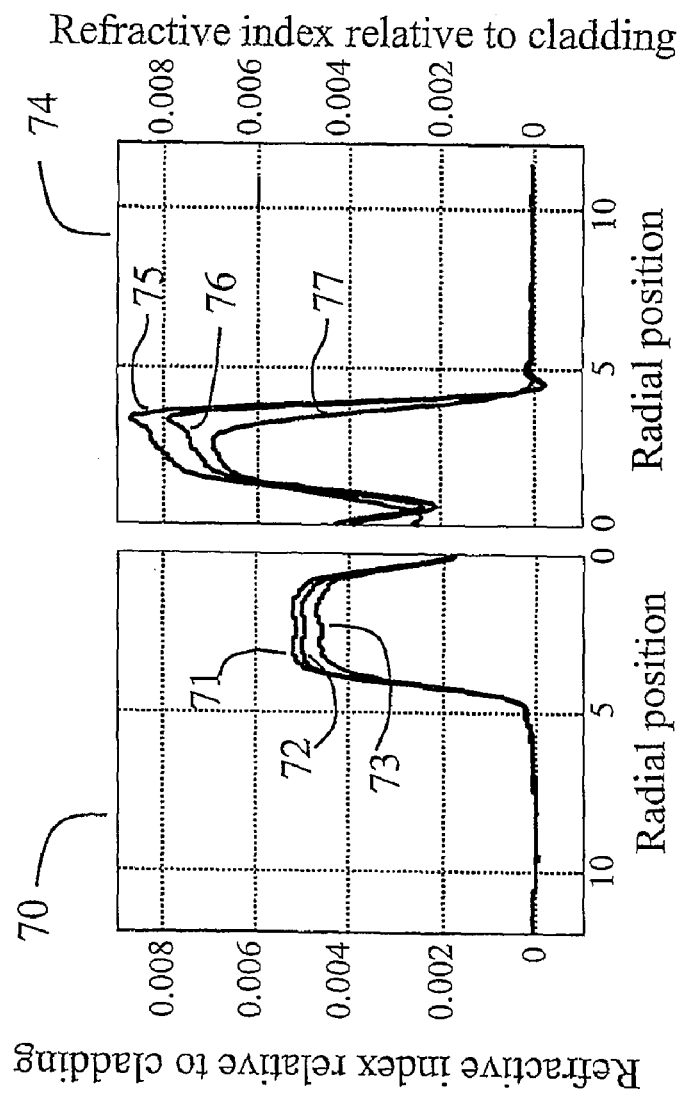
FIG. 5 is a graph of radial position and refractive index for two different optical fibers, according to an embodiment.

FIG. 5 is a graph of radial position and refractive index for two different optical fibers, according to an embodiment. A graph may be useful to compare information obtained using embodiments described herein for a substantially axisymmetric commercially available standard single-mode fiber 70 with a substantially axisymmetric commercially available photosensitive single-mode fiber 74. Horizontal and vertical axes of charts 70 and 74 show radial position and refractive index relative to surrounding refractive index matching oil, respectively. Refractive index measured using embodiments described herein at 493 nm, 520 nm, and 976 nm are shown for commercially available standard single-mode fiber by traces 71, 72, and 73 respectively. Refractive index measured using embodiments described herein at 493 nm, 520 nm, and 976 nm are shown for commercially available photosensitive fiber by traces 75, 76, and 77 respectively. It is seen that refractive index profile of photosensitive fiber varies more with wavelength than a standard single-mode fiber.

Embodiments in accordance with claimed subject matter may be used to measure material dispersion of an arbitrary optical fiber in a spatially resolved manner by fitting a curve to spectral variation of refractive index at a position in a fiber and differentiating. A fiber need not be cleaved for measurements performed by embodiments described herein, embodiments may be used to investigate or improve design or construction of optical fiber components that vary along their axis of propagation, such as optical fiber fusion splices, optical fiber tapers, optical fiber couplers, optical fiber pump combiners, or optical fiber gratings. Embodiments described herein may also be used to analyze spectral or spatial variation of refractive index of a fluid flowing inside a capillary tube.

While there has been illustrated and described what are presently considered to be example embodiments, it will be understood by those skilled in the art that various other modifications may be made, or equivalents may be substituted, without departing from claimed subject matter. Additionally, many modifications may be made to adapt a particular situation to teachings of claimed subject matter without departing from central concepts described herein. Therefore, it is intended that claimed subject matter not be limited to particular embodiments disclosed, but that claimed subject matter may also include all embodiments falling within the scope of appended claims, or equivalents thereof.

What is claimed is:

1. A method for measuring an optical fiber with a probe beam of a two beam optical interferometer, the method comprising:
   while illuminating a probe beam arm and a second beam arm of said two beam optical interferometer with broad spectrum, spatially incoherent light,
       shifting the phase of said broad spectrum, spatially incoherent light of said probe beam relative to the phase of said broad spectrum, spatially incoherent light in said second beam arm of said interferometer in a particular direction, and
       detecting fringe modulation responsive to said shifting phase using an array detector, wherein pixels in said array detector correspond to a particular spatial region in said optical fiber;
   performing a spectral decomposition of said detected fringe modulation along said particular direction of phase shift to determine relative phase at constituent optical wavelengths for spatial positions in said optical fiber; and
   determining a spatial distribution of the real part of a refractive index distribution in said optical fiber at one or more of said constituent optical wavelengths using said relative phase associated with said one or more of said constituent optical wavelengths.

2. The method of claim 1, wherein said shifting the phase of said broad spectrum, spatially incoherent light comprises continuously shifting the phase of said broad spectrum, spatially incoherent light.

3. The method of claim 2, wherein a portion of said optical fiber traversed by said probe beam is immersed in a fluid having a refractive index substantially similar to that of said optical fiber.

4. The method of claim 2, wherein said interferometer comprises a Mach-Zehnder interferometer and said optical fiber is imaged using an oil-immersion objective lens.

5. The method of claim 1, further comprising:
   measuring an optical path length of said optical fiber at multiple angles of rotation, wherein a total range of said multiple angles of rotation does not exceed 179 degrees;
   measuring said optical path lengths at multiple optical wavelengths at said multiple angles of rotation; and
   inverting said optical path lengths using computerized tomography to determine said refractive index distribution.

6. The method of claim 1, wherein said optical fiber comprises a capillary tube containing a flowing or stationary fluid.

7. The method of claim 1, wherein said optical fiber comprises an optical fiber coupler, optical fiber taper, fusion splice, fiber grating, or optical fiber pump combiner.

8. The method of claim 1 in which said optical fiber is carrying an optical signal during said determining said spatial distribution.

9. The method of claim 1, further comprising:
   measuring said relative phase or said refractive index distribution of said optical fiber more than once;
   translating a position of said optical fiber between said more than one measurements; and
   stitching together said relative phase or said refractive index distribution of said optical fiber measured more than once to determine information about a relatively large region of said optical fiber, wherein said large region is larger than a region measurable by a single, un-translated measurement of said relative phase or said refractive index distribution of said optical fiber.

10. A system for measuring an optical fiber, the system comprising:
   a two-beam interferometer including a probe beam arm and a second beam arm to measure said optical fiber oriented substantially perpendicular to a probe beam of said probe beam arm;
   a light source to provide broad spectrum, spatially incoherent light to said probe beam arm and said second beam arm:,
   a mechanism to shift the phase of said broad spectrum, spatially incoherent light of said probe beam relative to the phase of said broad spectrum, spatially incoherent light in said second beam arm of said interferometer in a particular direction;
   an array detector to detect fringe modulation resulting from said shifting phase; and
   a processor to numerically perform a spectral decomposition of said fringe modulation along said particular direction of said phase shift to determine relative phase at constituent optical wavelength for spatial positions in said optical fiber, and said processor to determine a spatial distribution of the real part of a refractive index distribution in said optical fiber at one or more of said constituent optical wavelengths using said relative phase associated with said one or more of said constituent optical wavelengths.

11. The system of claim 10, said mechanism to continuously shift the phase of said broad spectrum, spatially incoherent light of said probe beam.

12. The system of claim 11, wherein at least a portion of said optical fiber is immersed in a fluid whose refractive index substantially matches that of said optical fiber.

13. The system of claim 11, wherein said interferometer comprises a Mach-Zehnder interferometer and said optical fiber is imaged using an oil-immersion objective lens.

14. The system of claim 10, wherein a fluid whose refractive index substantially matches that of said optical fiber is located between surfaces of two opposing oil-immersion objective lenses, and said fluid location is maintained by surface tension.

15. The system of claim 10, wherein said phase of said broad spectrum, spatially incoherent light of said probe beam is shifted relative to said phase of said broad spectrum, spatially incoherent light in said second beam arm by translating an optical wedge through an arm of said interferometer.

16. The system of claim 10, wherein said broad spectrum, spatially incoherent light in one of said probe beam arm or said second beam arm of said interferometer is bent through a substantially 90 degree angle using a pentaprism or pentaprism equivalent element and said relative phase of said broad spectrum, spatially incoherent light in said one of said probe beam arm or said second beam arm is shifted by translating said pentaprism along an axis bisecting said 90 degree angle.

17. The system of claim 13, wherein optical sources having different spectral ranges are coupled to each of two input ports in said Mach-Zehnder interferometer.

18. The system of claim 13, further comprising different optical detectors to detect radiation emitted from two output ports of said Mach-Zehnder interferometer.

19. A system for measuring an optical fiber, the system comprising:
a two-beam interferometer measure said optical fiber oriented substantially perpendicular to a probe beam of said interferometer;
a mechanism to shift the phase of light in said probe beam relative to the phase of said light in a second beam of said interferometer in a particular direction;
an array detector to detect fringe modulation resulting from said shifting phase; and
a processor to numerically perform a spectral decomposition of said fringe modulation along said particular direction of said phase shift to determine relative phase at constituent optical wavelength for spatial positions in said optical fiber, said processor to determine a spatial distribution of the real part of a refractive index distribution in said optical fiber at one or more of said constituent optical wavelengths using said relative phase associated with said one or more of said constituent optical wavelengths, said mechanism to continuously shift the phase of light in said probe beam, wherein said interferometer comprises a Mach-Zehnder interferometer and said optical fiber is imaged using an oil-immersion objective lens, and wherein optical sources having different spectral ranges are coupled to each of two input ports in said Mach-Zehnder interferometer.

20. A system for measuring an optical fiber, the system comprising:
a two-beam interferometer measure said optical fiber oriented substantially perpendicular to a probe beam of said interferometer;
a mechanism to shift the phase of light in said probe beam relative to the phase of said light in a second beam of said interferometer in a particular direction;
an array detector to detect fringe modulation resulting from said shifting phase;
a processor to numerically perform a spectral decomposition of said fringe modulation along said particular direction of said phase shift to determine relative phase at constituent optical wavelength for spatial positions in said optical fiber, said processor to determine a spatial distribution of the real part of a refractive index distribution in said optical fiber at one or more of said constituent optical wavelengths using said relative phase associated with said one or more of said constituent optical wavelengths, said mechanism to continuously shift the phase of light in said probe beam, wherein said interferometer comprises a Mach-Zehnder interferometer and said optical fiber is imaged using an oil-immersion objective lens; and
different optical detectors to detect radiation emitted from two output ports of said Mach-Zehnder interferometer.

21. A method comprising:
shifting the phase of a broad spectrum of spatially incoherent light of a probe beam of an interferometer relative to the phase of the broad spectrum of spatially incoherent light in a second beam of the interferometer with respect to a waveguide in a direction while illuminating the probe beam and the second beam with the broad spectrum of spatially incoherent light;
detecting fringe modulation responsive to the shifting phase in a manner to correspond to a spatial region in the waveguide by spectral decomposition of the detected fringe modulation along the direction of the phase shift to determine relative phase at constituent wavelengths for spatial positions in the waveguide; and
determining a spatial distribution of the real part of a refractive index distribution in the waveguide at one or more of the constituent optical wavelengths using the relative phase.

22. An apparatus comprising: a non-transitory computing device including instruction to:
shift the phase of a broad spectrum of spatially incoherent light of a probe beam of an interferometer relative to the phase of the broad spectrum of spatially incoherent light in a second beam of the interferometer with respect to a waveguide in a direction while illuminating the probe beam and the second beam with the broad spectrum of spatially incoherent light;
detect fringe modulation responsive to the shifting phase in a manner to correspond to a spatial region in the waveguide by spectral decomposition of the detected fringe modulation along the direction of the phase shift to determine relative phase at constituent wavelengths for spatial positions in the waveguide; and
determine a spatial distribution of the real part of a refractive index distribution in the waveguide at one or more of the constituent optical wavelengths using the relative phase.

* * * * *